(12) United States Patent
Pettit et al.

(10) Patent No.: US 7,317,020 B2
(45) Date of Patent: Jan. 8, 2008

(54) ISOLATION AND STRUCTURE OF CRIBROSTATIN 6

(75) Inventors: George R. Pettit, Paradise Valley, AZ (US); John C. Knight, Phoenix, AZ (US)

(73) Assignee: Arizona Board of Regents, a body corporate of the State of Arizona, Tempe, AZ (US), acting for and on behalf of Arizona State University ( * ) Notice: Subject to any disclaimer, the term of this patent is extended or adjusted under 35 U.S.C. 154(b) by 3 days.

(21) Appl. No.: 10/546,468

(22) PCT Filed: Feb. 19, 2004

(86) PCT No.: PCT/US2004/005163

§ 371 (c)(1),
(2), (4) Date: Aug. 18, 2005

(87) PCT Pub. No.: WO2004/074248

PCT Pub. Date: Sep. 2, 2004

(65) Prior Publication Data

US 2006/0173032 A1 Aug. 3, 2006

Related U.S. Application Data

(60) Provisional application No. 60/449,167, filed on Feb. 20, 2003.

(51) Int. Cl.
*A61K 31/4745* (2006.01)
*C07D 471/06* (2006.01)

(52) U.S. Cl. .................................. 514/292; 546/84
(58) Field of Classification Search ................ 514/292; 546/84
See application file for complete search history.

(56) References Cited

U.S. PATENT DOCUMENTS

| 5,514,689 A | 5/1996 | Collins et al. |
| 6,159,985 A | 12/2000 | Liu et al. |
| 6,437,128 B1 | 8/2002 | Pettit et al. |

OTHER PUBLICATIONS

International Search Report for PCT/US04/05163 dated Aug. 9, 2004.
Written Opinion of the International Search Authority for PCT/US04/05163 dated Sep. 2, 2004.
Pettit et al., "Antineoplastic Agents. 485. Isolation and Structure of Cribrostatin 6, a Dark Blue Cancer Cell Growth Inhibitor from the Marine Sponge *Cribrochalina* sp.", *J. Nat. Prod.*, 66:544-547, 2003.

*Primary Examiner*—Charanjit S. Aulakh
(74) *Attorney, Agent, or Firm*—Fennemore Craig, P.C.

(57) ABSTRACT

Cribrostatin 6, a dark blue cancer cell growth inhibiting constituent of the Republic of Maldives marine sponge Cribrochalina sp. has been isolated, and its structure (shown below) elucidated, based on a combination of RMS, high field (500 MHz, HMBC, and GOESY experiments) 15N, $^1$H- and 13C NMR, and X-ray crystal structure analyses. Cribrostatin 6 also was found to inhibit the growth of a number of pathogenic bacteria and fungi.

7 Claims, 1 Drawing Sheet

1, Cribrostatin 4

2, Cribrostatin 5

3, Cribrostatin 6

4, Cribrostatin 3

5, Cribrostatin 1

6, Cribrostatin 2

US 7,317,020 B2

ISOLATION AND STRUCTURE OF CRIBROSTATIN 6

RELATED APPLICATION DATA

This application is the U.S. national stage of PCT/US04/05163 filed on Feb. 19, 2004, which is based on and claims the benefit of U.S. Provisional Patent Application No. 60/449,167 filed on Feb. 20, 2003, which is incorporated herein in its entirety by this reference.

INTRODUCTION

Financial assistance for this invention was provided by the United States Government, Division of Cancer Treatment and Diagnosis, National Cancer Institute, Department of Health and Human Services Outstanding Investigator Grant Numbers R01-CA9044-01 and CA44344-05-1-12; the Arizona Disease Control Research Commission; and private contributions. Thus, the United States Government has certain rights in this invention.

FIELD OF THE INVENTION

This invention relates to the isolation from natural sources, and elucidation of the structure of, a compound having antineoplastic, antibacterial and antifungal properties.

BACKGROUND OF THE INVENTION

Marine porifera have continued to be an increasingly important source of new nitrogen heterocyclic compounds with significant biological activities. Recent examples include the cytotoxic constituents pateomine (*Mycale* sp.), a pyridine betaine (*Microcosmus vulgaris*), topsentin B2 (*Rhaphisia lacazei*), asmarine A (*Raspailia* sp.), cyclic guanidines (*Monanchora* sp.), the antiviral dragmacidin F (*Halicortex* sp.) and the isolation and structure determination of cribrostatins 4 (1) and 5 (2) from the Republic of Maldives blue-colored sponge *Cribrochalina* sp. (West, L.; et al., *J. Org. Chem.* 2000, 65, 445-449; Aiello, A., et al., *J. Nat. Prod.* 2000, 63, 517-519; Casapullo, A., et al., *J. Nat. Prod.* 2000, 63, 447-451; Yosief, T., et al., *J. Nat. Prod.* 2000, 63, 299-304; Braekman, J., et al., *J. Nat. Prod.* 2000, 63, 193-196; Cutignano, A., et al., *Tetrahedron* 2000, 56, 3743-3748, Pettit, G., et al., *J. Nat. Prod.* 2000, 6, 793-798.)

SUMMARY OF THE INVENTION

The present invention relates to the elucidation of the molecular structure for a novel compound denominated Cribrostatin 6, as well as to a method for isolating the compound Cribrostatin 6 from the Marine organism *Cribrochalina* sp. Cribrostratin 6 exhibits antineoplastic, antibacterial and antifungal properties. Accordingly, the invention also relates to the use of Cribrostatin 6 as a pharmaceutical agent for the treatment of neoplastic disease, as well as for the treatment of bacterial and fungal infections.

DETAILED DESCRIPTION OF THE INVENTION

Figure 1:
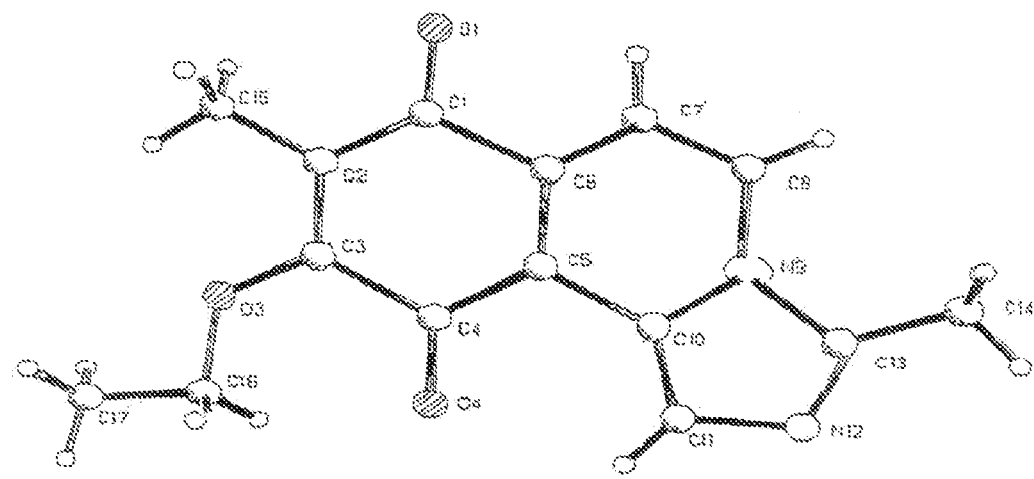
FIG. 1 illustrates the solid-state structure of Cribrostatin 6.
Figure 2:
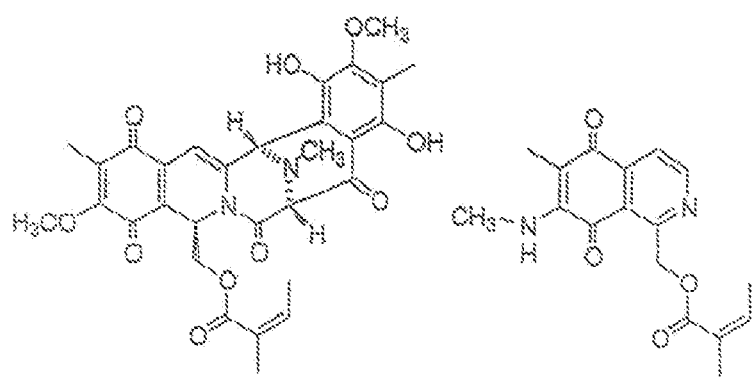
FIG. 2 illustrates the chemical structures of Cribrostatins 1, 2, 3, 4, 5 and 6.
Figure 2:
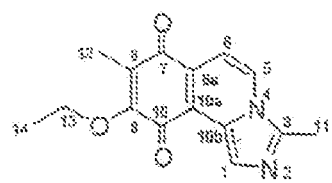
Figure 2:
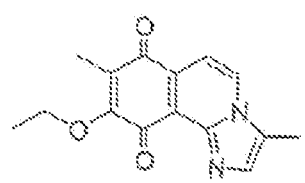
Figure 2:
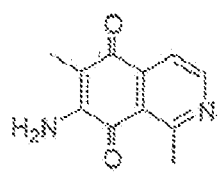
Figure 2:
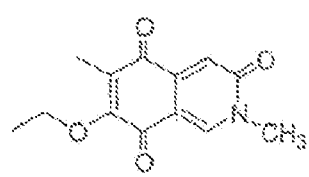

Earlier we had observed a number of biologically active blue to black colored fractions arising during P388 lymphocytic leukemia guided separations of a 195 g dichloromethane-soluble portion of the extract obtained from 350 kg (wet wt.) of *Cribrochalina* sp. The cancer cell growth (P-388) inhibitory dark-colored fractions were finally separated by a successive series of gel permeation and partition chromatographic techniques on Sephadex LH-20. That sequence was followed by high-speed countercurrent distribution using an Ito Coil-Planet centrifuge to afford 88 mg of a dark-blue constituent (P388 $ED_{50}$ 0.3 µg/ml), designated cribrostatin 6 (3). Owing to difficulties in unequivocally deducing the structure of this interesting substance based on spectral evidence, attempts were made at various times over a ten year period to reach a correct solution and/or to produce crystals suitable for X-ray structure determination. We were eventually pleased to find that cribrostatin 6 (3) would crystallize from acetone following long cold storage of the solution. To follow is a summary of the spectral and X-ray crystallographic interpretation that completed a correct structural assignment for cribrostatin 6 (3).

Results and Discussion

The molecular formula of cribrostatin 6 (3) was established as $C_{15}H_{14}N_2O_3$ by HRMS, using an APCI inlet system. Inspection of the $^1H$ and APT NMR spectra indicated the presence of three methyls, one methylene, three methines and eight quaternary carbons. Protonated carbons were assigned using a HMQC experiment. The APT spectrum indicated that four of the carbons were oxygenated and suggested the presence of the quinone. An HMBC experiment allowed placement of the C-9 ethoxy (H-13 to C-9) and C-8 methyl (H-12 to C-7, 8, and 9) groups and established the positions of the quaternary carbons at C-8 and 9 as well as the carbonyl carbons at C-7 and 10, which were assigned by analogy with known isoquinolinequinones such as the Saframycins. (Cooper, R., et al., *Antibiotics* 1985, 38, 24-30). This accounted for five of the ten degrees of unsaturation determined from the molecular formula. The nature of the B ring was established by 1H-1H COSY, which indicated the presence of a double bond. The HMBC spectrum showed connectivities from the proton at H-6 to C-6a, 7 and 10a as well as establishing the position of the double bond at Δ, which was confirmed by HMBC correlations from H-5 to C-6 and 6a. (Braekman, J., et al., *J. Nat. Prod.* 2000, 63, 193-196; Cutignano, A., et al., *Tetrahedron* 2000, 56, 3743-3748.) The remaining three degrees of unsaturation and the fragment $C_3H_4N_2$ suggested an imidazo-partial structure for a C ring. The overall structure was determined by X-Ray diffraction on a small needle-shaped crystal. Although the overall connectivity could be readily established, the low observed data-to-parameter ratio did not permit a clear distinction between structures 3 and 4. Analogy to previous cribrostatin-related compounds (cf. 1, 2) gave the location of one of the N atoms at position 4 with reasonable certainty (Pettit, G., et al., *J. Nat. Prod.* 2000, 6, 793-798; Pettit, G., et al., *Can. J. Chem.* 1992, 70, 1170-1175), but conclusive structural assignment as 9-ethoxy-3,8-dimethyl-imidazo[5,1-a]isoquinoline-7, 10-dione (3) required further, more detailed analysis of earlier and new NMR data.

Examination of the HMBC spectrum showed correlations from H5 to C-3 and C10b and implied placement of a nitrogen at position 4. A strong correlation from the remaining methine proton to C-3 suggested position 1 with the remaining nitrogen at position 2. An additional correlation from H-11 to C-3 located the remaining methyl group (δ2.75p) at C-3. A DPFGSENOE (GOESY) experiment demonstrated NOE enhancement between H-5 and H-11 that would be consistent with either structure 3 or 4, but gave no indication of an enhancement between H-2 and H-11, that would be expected to exist in structure 4 (Stonehouse, J., et al., *J. Amer. Chem. Soc.* 1994, 116, 6037-6038). Measurement of $^{15}N$-$^1H$ HMBC showed two strong 3-bond correlations from the methyl protons H11 to both nitrogens N2 and N4. HMBC correlations were observed H5 and H6 to N4, but not N2. H1 showed weak correlations to both N2 and N4. Only structure 3 is consistent with these results.

In addition to cancer cell growth inhibition of murine P388 lymphocytic leukemia and human cancer cell lines (see Table II), cribrostatin 6 exhibited antimicrobial activity against numerous antibiotic-resistant Gram-positive bacteria and patlhogenic fungi (see Table III). The only Gram-negative bacterium of those tested which was inhibited by cribrostatin 6 was *Neisseria gonorrhoeae*. Cribrostatin 2 has an antimicrobial profile similar to cribrostatin 6, while cribrostatins 1, 3, 4 and 5 have antibacterial but not antifungal activities. (Pettit, G., et al., *J. Nat. Prod.* 2000, 6, 793-798). Thus, the inventors believe that the cribrostatins, particularly cribrostatin 6, warrant further investigation as antibacterial and/or antifungal agents.

Recently, two phosphorylated sterol sulfates were isolated from a *Cribrochalina* sp. and found to be membrane-type metalloproteinase (MT1-MMP) inhibitors. (Fujita, M., et al., *Tetrahedron* 2001, 57, 3885-3890.) That advance extends the structural variety of *Cribrochalina* genus cell growth regulatory constituents that so far range from acetylenic alcohols to quinones (cf. 3) and peptides. (Hallock, Y., et al., *J. Nat. Prod.* 1995, 58, 1801-1807; Garcia, J., et al. *Tetrahedron: Asymmetry* 1999, 10, 2617-2626; Sharma, A.; et al., S. *Tetrahedron: Asymmetry* 1998, 9, 2635-2639; Pettit, G., et al., *J. Nat. Prod.* 2000, 6, 793-798; Pettit, G., et al., *Can. J Chem.* 1992, 70, 1170-1175; Yeung, B., et al., *J. Org. Chem.* 1996, 61, 7168-7173.)

Experimental Section

General Experimental Methods. Except as noted, the general experimental procedures employed in our original investigations of the *Cribrochalina* sp. were continued here. For discussion of these original investigations, see Pettit, G., et al., *J. Nat. Prod.* 2000, 6, 793-798; and Pettit, G., et al., *Can. J Chem.* 1992, 70, 1170-1175, which are incorporated herein by reference. NMR spectra were recorded using a Varian Inova system equipped with a 5 mm triple resonance triaxial PFG probe at 500 MHz for $^1H$ and 125 MHz for $^{13}C$, and 50.65 MHz for $^{15}N$. $^{15}N$-$^1H$ gradient HMBC experiments were performed on 2.2 mg of sample dissolved in 100 µl CDCl$_3$ using a Shigemi 3 mm NMR tube susceptibility matched to CDCl$_3$, a Nalorac 3 mm $^1H\{^{15}N$-$^{31}P\}$ indirect-detection probe and delays optimized for coupling constants of 90 Hz (1-bond) and 5 Hz (multiple-bond). The $^{15}N$ spectra were referenced to formamide (112 pm downfield of liquid ammonia). (Martin, G. et al., *J. Nat. Prod.* 2000, 63, 543-585.) The $^1H$ NMR and $^{13}C$ NMR spectra were referenced to residual solvent signals at 7.25 and 77.0 ppm for CDCl$_3$. HRMS data was obtained using a JEOL LCMate magnetic sector instrument in the APCI mode, calibrated using a polythylene glycol reference mixture. The X-Ray data collection was accomplished using a Bruker AXS 6000 diffractometer.

Isolation of Cribrostatin 6 (1). The blue marine sponge *Cribrochalina* sp. was collected and extracted as known to one of skill in the art, as described in Pettit, G., et al., *J. Nat. Prod.* 2000, 6, 793-798 and Pettit, G., et al., *Can. J. Chem.* 1992, 70, 1170-1175, which is incorporated herein by reference. Fractionation of the extract, guided by the blue color, and the screening results obtained using the murine P-388 lymphocytic leukemia cell line, was carried out on columns of Sephadex LH-20, eluted successively with a.) CH$_3$OH; b.) CH$_2$Cl$_2$—CH$_3$OH (3:2); c.) hexane-toluene-CH$_3$OH (3:1:1); and d.) hexane/i-PrOH-CH$_3$OH (8:1:1). In preparation for a separation using high-speed countercurrent distribution on an Ito Coil-Planet centrifuge, the blue fraction from the previous column was triturated with the upper (less polar) phase of the system hexane-EtOAc-CH$_3$OH-water (700:300:150:60), and the solution was filtered. The sparingly-soluble material thus obtained (35.7 mg) proved to be the same as the solid isolated from the principal blue fraction from the countercurrent run (53 mg). The two were combined and recrystallized from acetone to afford dark-blue needles: mp 169-171° C.; P-388 ED$_{50}$ 0.3 µg/ML; $\lambda_{max}$ 203 (26,758), 266 (24,432), 323 (5597), 552 (1479); IR $v_{max}$ 2920, 1660, 1620, 1605, 1522, 1170 cm$^{-1}$; $^1H$ and $^{13}C$-NMR, see Table I; LREIMS (m/z) 270, 242, 214, 185, 172, 157, 145, 116; HRMS (APCI$^+$) 271.10968 (calcd for (M+H)$^+$ ion C$_{15}$H$_{15}$N$_2$O$_3$, 271.10828 error 5.2 ppm).

Crystal Structure of Cribrostatin 6 (3). All data including atomic coordinates, thermal parameters, bond distances, angles, and observed and calculated structure factors have been deposited in the Cambridge Crystallographic Data Centre and can be obtained, free of charge, on application to the Director, CCDC, 12 Union Road, Cambridge CB2 1EZ, UK (fax: +44-(0)1223-336003 or e-mail: deposit@ccdc.cam.ac.uk). A very small, dark-blue needle obtained via slow evaporation of an acetone solution, with approximate dimensions of (0.05×0.05×0.20 mm), was mounted on the tip of a glass fiber. An initial set of cell constants was calculated from reflections harvested from three sets of 60 frames at 298(2) K on a Bruker 6000 diffractometer. Cell parameters indicated an orthorhombic space group. Subsequent data collection, using 30 second scans/frame and 0.396° steps in Ω, was conducted in such a manner as to completely survey a complete hemisphere of reflections. This resulted in >93% coverage of the total reflections possible to a resolution of 0.83. A total of 10229 reflections were harvested from the total data collection and final cell constants were calculated from a set of 332 strong, unique reflections. Subsequent statistical analysis of the complete reflection data set using the XPREP program indicated the space group was Pca2$_1$. The XPREP program is an automatic space determination program included in the SHELXTL-NT-Version 5.10 (1997), which an integrated suite of programs for the determination of crystal structures from diffraction data, that is available from Bruker AXS, Inc., Madison, Wis. 53719, USA. This package includes, among others, XPREP, SHELXS (a structure solution program via Patterson or direct methods), and SHELXL (structure refinement software).

Crystal data: C$_{15}$H$_{14}$N$_2$O$_3$, a=15.414(15), b=11.532(11), c=7.201(7) Å, V=1280(2) Å$^3$, λ=(Cu Kα)=1.54178 Å, µ (Cu K)=0.817 mm$^{-1}$, ρc=1.403 g cm$^{-3}$ for Z=4 and M$_r$=270.28, F (000)=568. After data reduction, merging of equivalent reflections and rejection of systematic absences, 1885 unique reflections remained (R$_{int}$=0.5248), of which 315 were considered observed (I$_o$>2 (I$_o$)) and were used in the subsequent structure solution and refinement. An absorption correction was applied to the data with SADBS. (Blessing, R., *Acta Cryst.*, 1995, A51, 33-8.) Direct methods structure determination and refinement were accomplished with the SHELXTL NT ver.V5.10 suite of programs. All non-hydrogen atoms for cribrostatin 6 (3) were located using the default settings of that program. Although the overall connectivity of the non-hydrogen atoms in quinone 3 could be readily established from the X-ray data, the low observed data-to-parameter ratio did not allow a completely unambiguous assignment of the two nitrogen atoms. The location of one of the N atoms at position 9 (FIG. 1; X-ray numbering system) was known with reasonable certainty (due to analogy to previous cribrostatin related compounds), the position of the second N atom was less certain, with positions 11 and 12 both being likely candidates. Refinement of each of these possible isomeric structures (i.e., structures 3 or 4) resulted in nearly identical residual $R_1$ values (0.0982 vs 0.1002, respectively). Although the former (3) was slightly favored by these results, the final, conclusive structural assignment was based on observed $^{15}$N-NMR experiments. Since the quality of data precluded the direct determination of hydrogen atom positions, the remaining hydrogen atom coordinates were calculated at optimum positions using the program SHELXL. These latter atoms were assigned thermal parameters equal to either 1.2 or 1.5 (depending upon chemical type) of the Uiso value of the atom to which they were attached, then both coordinates and thermal values were forced to ride that atom during final cycles of refinement. All non-hydrogen atoms were refined anisotropically in a full-matrix least-squares refinement process. The final standard residual $R_1$ value for the model shown in FIG. 1 was 0.0982 (for observed data) and 0.3817 (for all data). The corresponding Sheldrick R values were $wR_2$ of 0.2174 and 0.2741, respectively. The difference Fourier map showed insignificant residual electron density; the largest difference peak and hole being +0.255 and −0.252 e/Å$^3$, respectively. Final bond distances and angles were all within acceptable limits.

Cancer Cell Growth Inhibition

Compounds were screened against a panel of human cancer cell lines and mouse cell lines as is shown in Table II. Cribrostatin 6 exhibited cancer cell growth against all lines illustrated.

Antimicrobial Susceptibility Testing

Compounds were screened against bacteria and fungi according to established broth microdilution susceptibility assays, pursuant to the National Committee for Clinical Laboratory Standards, Methods for Dilution Antimicrobial Susceptibility Tests for Bacteria that Grow Aerobically, Approved Standard M7-A4, Wayne, Pa.: NCCLS, 1997, and the National Conmnittee for Clinical Laboratory Standards, Reference Method for Broth Dilution Antifungal Susceptibility Testing of Yeasts, Approved Standard M27-A, Wayne, Pa.: NCCLS, 1997. The results of such screening are shown in Table III. The minimum inhibitory concentration was defined as the lowest concentration of compound that inhibited all visible growth of the test organism (optically clear). Assays were repeated on separate days.

ADMINISTRATION

Dosages

The dosage of the presently disclosed compounds to be administered to humans and other animals requiring treatment will depend upon numerous factors, including the identity of the neoplastic disease or microbial infection; the type of host involved, including its age, health and weight; the kind of concurrent treatment, if any; the frequency of treatment and therapeutic ratio. Hereinafter are described various possible dosages and methods of administration, with the understanding that the following are intended to be illustrative only, and that the actual dosages to be administered, and methods of administration or delivery may vary therefrom. The proper dosages and administration forms and methods may be determined by one of skill in the art.

Illustratively, dosage levels of the administered active ingredients are: intravenous, 0.1 to about 20 mg/kg; intramuscular, 1 to about 50 mg/kg; orally, 5 to about 100 mg/kg; intranasal instillation, 5 to about 100 mg/kg; and aerosol, 5 to about 100 mg/k of host body weight.

Expressed in terms of concentration, an active ingredient can be present in the compositions of the present invention for localized use about the cutis, intranasally, pharyngolaryngeally, bronchially, intravaginally, rectally, or ocularly in concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient. Other dosage forms known in the art may be used.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration.

The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal installation, a fluid unit dosage form is prepared utilizing an active ingredient and a suitable pharmaceutical vehicle, preferably P.F. water, a dry powder, can be formulated when insulation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable. The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic and/or antimicrobial agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. The following are examples of several dosage forms, in which the notation "active ingredient" signifies Cribrostatin 6.

COMPOSITION "A"

Hard-Gelatin Capsules

One thousand two-piece hard gelatin capsules for oral use, each capsule containing 200 mg of an active ingredient are prepared from the following types and amounts of ingredients:

| | |
|---|---|
| Active ingredient, micronized | 20 g |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 5, 25, and 50 mg amounts by substituting 5 g, 25 g and 50 g of an active ingredient for the 20 g used above.

COMPOSITION "B"

Soft Gelatin Capsules

One-piece soft gelatin capsules for oral use, each containing 20 mg of an active ingredient, finely divided by means of an air micronizer, are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 20 mg of an active ingredient, are prepared from the following types and amounts of ingredients:

| | |
|---|---|
| Active ingredient, micronized | 20 g |
| Lactose | 300 g |

-continued

| | |
|---|---|
| Corn starch | 50 g |
| Magnesium stearate | 4 g |
| Light liquid petrolatum | 5 g |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 20 mg of the active ingredient.

The foregoing tablets are useful for treating a neoplastic disease by the oral administration of one or two tablets one to four times a day.

Using the procedure above, tablets are similarly prepared containing an active ingredient in 25 mg and 10 mg amounts by substituting 25 g and 10 g of an active ingredient for the 20 g used above.

COMPOSITION "D"

Oral Suspension

One liter of an aqueous suspension for oral use, containing in each teaspoonful (5 ml) dose, 50 mg of an active ingredient, is prepared from the following types and amounts of ingredients:

| | |
|---|---|
| Active ingredient, micronized | 1 g |
| Citric acid | 2 g |
| Benzoic acid | 1 g |
| Sucrose | 790 g |
| Tragacanth | 5 g |
| Lemon Oil | 2 g |
| Deionized water, q.s. | 1000 ml |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a neoplastic disease at a dose of 1 teaspoonful (15 ml) three times a day.

COMPOSITION "E"

Parenteral Product

A sterile aqueous suspension for parenteral injection, containing 3 mg of an active ingredient in each milliliter for treating a neoplastic disease, is prepared from the following types and amounts of ingredients:

| | |
|---|---|
| Active ingredient, micronized | 3 g |
| POLYSORBATE 80 | 5 g |
| Methylparaben | 2.5 g |
| Propylparaben | 0.17 g |
| Water for injection, q. s. | 1000 ml. |

All the ingredients, except the active ingredient, are dissolved in the water and the solution sterilized by filtration. To the sterile solution is added the sterilized active ingredient, finely divided by means of an air rnicronizer, and the final suspension is filled into sterile vials and the vials sealed.

The composition so prepared is useful for treating a neoplastic disease at a dose of 1 milliliter (1 ml) three times a day.

COMPOSITION "F"

Suppository, Rectal and Vaginal

One thousand suppositories, each weighing 2.5 g and containing 20 mg of an active ingredient are prepared from the following types and amounts of ingredients:

| | |
|---|---|
| Active ingredient, micronized | 1.5 g |
| Propylene glycol | 150 g |
| Polyethylene glycol #4000, q.s. | 2,500 g |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One liter of a sterile aqueous suspension for intranasal instillation, containing 2 mg of an active ingredient in each milliliter, is prepared from the following types and amounts of ingredients:

| | |
|---|---|
| Active ingredient, micronized | 1.5 g |
| POLYSORBATE 80 | 5 g |
| Methylparaben | 2.5 g |
| Propylparaben | 0.17 g |
| Deionized water, q.s. | 1000 ml. |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times per day.

An active ingredient can also be present in the undiluted pure form for use locally about the cutis, intranasally, pharyngolaryngeally, bronchially, or orally.

COMPOSITION "H"

Powder

Five grams of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of an active ingredient in bulk form is finely divided by means of an air micronizer. The micronized powder is divided into individual doses of 20 mg and packaged.

The foregoing powders are useful for treating a neoplastic disease, by the oral administration of one or two powders suspended in a glass of water, one to four times per day.

COMPOSITION "J"

Insufflation

One hundred grams of an active ingredient in bulk form is finely divided by means of an air micronizer. The foregoing composition is useful for treating a neoplastic disease, by the inhalation of 30 mg one to four times a day. It is of course understood that such modifications, alterations and adaptations as will readily occur to the artisan confronted with this disclosure are intended within the spirit of the present invention.

TABLE I

High Field (500 MHz) NMR Assignments for Cribrostatin 6 (3), (3,8-dimethyl-9-ethoxy-imidazo[5,1-a]isoquinoline-7,10-dione) in $CDCl_3$

| Position | $^1H$ δ(mult, J, #H) | $^{13}C$ and $^{15}N$ | HMBC j1xh = 140, jnxh = 8 | COSY | GOESY mix = .3 |
|---|---|---|---|---|---|
| 1 | 8.29s, 1H | 125.68 | C-3 | | |
| 2 | | | | | |
| 3 | | 137.64 | | | |
| 4 | | | | | |
| 5 | 7.90d, 7.5Hz, 1H | 124.73 | C-3, C-6, C-6a | H-6 | H-6, H-11 |
| 6 | 7.26d, 7.5Hz, 1H | 107.73 | C-6a, C-7, C-10a | H-5 | |
| 6a | | 125.00 | | | |
| 7 | | 184.86 | | | |
| 8 | | 130.06 | | | |
| 9 | | 156.16 | | | |
| 10 | | 180.58 | | | |
| 10a | | 123.49 | | | |
| 10b | | 123.87 | | | |
| 11 | 2.75s, 3H | 12.57 | C-3 | | H-5 |
| 12 | 2.06s, 3H | 9.15 | C-7, C-8, C-9 | | |
| 13 | 4.40q, 6.9Hz, 2H | 69.64 | C-9, C-14 | H-14 | |
| 14 | 1.41t, 6.8Hz, 3H | 15.97 | C-13 | H-13 | |
| N-4 | | 189.5 | | | |
| N-2 | | 273.9 | | | |

TABLE II

Cribrostatin 6 (3) Inhibitory Activity ($GI_{50}$, μg/ml) Against a Panel of Human Cancer Cell Lines and Mouse Leukemia

| Cell Type | Cell Line | Cribrostatin-6 |
|---|---|---|
| Pancreas-adenocarcinoma | BXPC-3 | >1 |
| Breast-adenocarcinoma | MCF-7 | 0.21 |
| CNS Glioblastoma | SF-268 | 0.24 |
| Lung-NSC | NCI-H460 | >1 |
| Colon-adenocarcinoma | KM20L2 | >1 |
| Prostate | DU-145 | 0.38 |
| Mouse Leukemia | P388 | 0.29 |

TABLE III

Antimicrobial Activities of Cribrostatin 6.

| Microorganism | Minimum Inhibitory Concentration (μg/ml) |
|---|---|
| *Candida albicans* (ATCC 90028) | 64 |
| *Cryptococcus neoformans* (ATCC 90112) | 2 |
| *Micrococcus luteus* (Presque Isle 456) | 16 |
| *Staphylococcus aureus* (ATCC 29213) | 16 |
| Methicillin-resistant *S. aureus* (clinical isolate) | 16 |
| *Enterococcus faecalis* (ATCC 29212) | 32 |
| Vancomycin-resistant *E. faecalis* (clinical isolate) | 32 |
| *Bacillus subtilis* (clinical isolate) | 2 |
| *Streptococcus pneumoniae* (ATCC 6303) | 0.5 |
| Penicillin-resistant *S. pneumoniae* (clinical isolate) | 2 |
| Invasive *S. pneumoniae* (clinical isolate) | 1 |
| Group A *Streptococcus* (clinical isolate) | 16 |
| *Stenotrophomonas maltophilia* (ATCC 13637) | >64 |
| *Escherichia coli* (ATCC 25922) | >64 |
| *Enterobacter cloacae* (ATCC 13047) | >64 |
| *Neisseria gonorrhoeae* (ATCC 49226) | 0.0625 |

What we claim is:

1. A compound and furthermore 9-ethoxy-3,8-dimethyl-imidazo[5,1-a]isoquinoline-7,10-dione.

2. The compound of claim 1, having the following high filed (500 MHz) NMR assignments in $CDCl_3$

| Position | $^1H$ δ(mult, J, #H) | $^{13}C$ and $^{15}N$ | HMBC j1xh = 140, jnxh = 8 | COSY | GOESY mix = .3 |
|---|---|---|---|---|---|
| 1 | 8.29s, 1H | 125.68 | C-3 | | |
| 2 | | | | | |
| 3 | | 137.64 | | | |
| 4 | | | | | |
| 5 | 7.90d, 7.5Hz, 1H | 124.73 | C-3, C-6, C-6a | H-6 | H-6, H-11 |
| 6 | 7.26d, 7.5Hz, 1H | 107.73 | C-6a, C-7, C-10a | H-5 | |
| 6a | | 125.00 | | | |
| 7 | | 184.86 | | | |
| 8 | | 130.06 | | | |
| 9 | | 156.16 | | | |
| 10 | | 180.58 | | | |
| 10a | | 123.49 | | | |
| 10b | | 123.87 | | | |
| 11 | 2.75s, 3H | 12.57 | C-3 | | H-5 |
| 12 | 2.06s, 3H | 9.15 | C-7, C-8, C-9 | | |
| 13 | 4.40q, 6.9Hz, 2H | 69.64 | C-9, C-14 | H-14 | |
| 14 | 1.41t, 6.8Hz, 3H | 15.97 | C-13 | H-13 | |
| N-4 | | 189.5 | | | |
| N-2 | | 273.9. | | | |

3. A composition comprising the compound of claim 1 and a pharmaceuticaly acceptable carrier therefor.

4. A method for treating neoplastic disease selected from the group consisting of pancreatic cancer, breast cancer, central nervous system cancer,lung cancer colon cancer, prostate cancer and leukemia, comprising administering a therapeutically effective amount of the compound of claim 1 to a human or animal subject.

5. A method for treating bacterial infections selected from the group consisting of *Micrococcus lutes, Staphylococcus aureus, Enterococcus faecalis, Bacillus sublilis, Streptococcus pneumoniae*, Group A *Streptococcus, Stenotrophonionas maltophilia, Escherichia coli, Enterobacter cloacae* and *Neisseria gonorrhoeae*, comprising administering a therapeutically effective amount of the compound of claim 1 to a human or animal subject.

6. A method for treating fungal infections selected from the group consisting of *Candida albicans* and *Cryptococcus neoformans*, comprising administering a therapeutically effective amount of the compound of claim 1 to a human or animal subjet.

7. A method for purifying cribrostating 6 (9-ethoxy-3,8-dimethyl-imidazo[5,1-a]isoquinoline-7,10-dione) by:
   (a) fractionating extract of blue marine sponge *Cribochalina* sp. Via successive elutions with $CH_3OH$, $CH_2Cl_2$—$CH_3OH$ (3:2), hexane-toluene —$CH_3OH$ (3:1:1) and hexane/i-PrOH—$CH_3OH$ (8:1:1),
   (b) triturating the blue fraction resulting from step (a) with less polar phase of the system hexane-EtOAc—$CH_3OH$-water (700:300:150:60),
   (c) filtering the solution and (d) obtaining a solid.

* * * * *

UNITED STATES PATENT AND TRADEMARK OFFICE
CERTIFICATE OF CORRECTION

PATENT NO. : 7,317,020 B2 Page 1 of 1
APPLICATION NO. : 10/546468
DATED : January 8, 2008
INVENTOR(S) : George R. Pettit et al.

It is certified that error appears in the above-identified patent and that said Letters Patent is hereby corrected as shown below:

Column 12, claim 2, line 40, "filed" should be changed to --field--.
Column 13, claim 4, line 5, "lung cancer" should be changed to --lung cancer,--.
Column 13, claim 5, line 11, "lutes" should be changed to --luteus--.
Column 13, claim 5, line 12, "subilis" should be changed to --subtilis--.
Column 13, claim 5, line 13, "Stenotrophonionas" should be changed to --Stenotrophomonas--.
Column 14, claim 7, line 6, "cribrostating" should be changed to --cribrostatin--.

Signed and Sealed this

Twelfth Day of May, 2009

JOHN DOLL
*Acting Director of the United States Patent and Trademark Office*